United States Patent
Westphal et al.

(10) Patent No.: US 11,406,614 B2
(45) Date of Patent: Aug. 9, 2022

(54) COMPOSITION COMPRISING EPA AND DHA FOR AN ENHANCED EFFICACY OF ANTICANCER AGENTS

(71) Applicant: Fresenius Kabi Deutschland GmbH, Bad Homburg (DE)

(72) Inventors: Martin Westphal, Bad Homburg (DE); Edmundo Brito De La Fuente, Friedrichsdorf (DE); Crispulo Gallegos-Montes, Bad Homburg (DE); Silke Baasner, Schöneck (DE); Stefanie Honndorf, Bad Homburg (DE); Lida Quinchia, Bad Homburg (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 189 days.

(21) Appl. No.: 16/341,118

(22) PCT Filed: Oct. 5, 2017

(86) PCT No.: PCT/EP2017/075352
§ 371 (c)(1),
(2) Date: Apr. 11, 2019

(87) PCT Pub. No.: WO2018/069145
PCT Pub. Date: Apr. 19, 2018

(65) Prior Publication Data
US 2020/0306215 A1    Oct. 1, 2020

(30) Foreign Application Priority Data
Oct. 11, 2016  (EP) .................... 16193256

(51) Int. Cl.
*A61K 31/513*    (2006.01)
*A61K 31/4745*   (2006.01)
*A61K 31/202*    (2006.01)
*A61K 47/12*     (2006.01)
*A61P 35/00*     (2006.01)

(52) U.S. Cl.
CPC ........ *A61K 31/202* (2013.01); *A61K 31/4745* (2013.01); *A61K 31/513* (2013.01); *A61K 47/12* (2013.01); *A61P 35/00* (2018.01)

(58) Field of Classification Search
CPC .............. A61K 31/513; A61K 31/4745; A61K 31/202; A61K 47/12; A61P 35/00
See application file for complete search history.

(56) References Cited

FOREIGN PATENT DOCUMENTS

| WO | 2007075841 A1 | 7/2007 |
| WO | 2012033538 A1 | 3/2012 |
| WO | 2015113986 A1 | 8/2015 |

OTHER PUBLICATIONS

D'Eliseo D. et al., "Omega-3 Fatty Acids and Cancer Cell Cytotoxicity: Implications for Multi-Targeted Cancer Therapy," Journal of Clinical Medicine, Jan. 26, 2016, vol. 26, No. 5(2):15, 29 pages.
Gavhane Y.N., et al. , "Solid Tumors: Facts, Challenges and Solutions," International Journal of Pharma Sciences and Research (IJPSR), vol. 2(1), pp. 1-12, Chennai: K. Sivakumar, India.
https://www.chemicalbook.com/ChemicalProductProperty_EN_CB5128501.htm, accessed Oct. 25, 2021, 2 pages.
Kumar, Nagi B., "Nutritional Management of Cancer Treatment Effects," Springer Science & Business Media, Springer Heidelberg Dordrecht, London/New York, 2012, pp. 70-71.
Morland, S. L., et al., (2016). N-3 polyunsaturated fally acid supplementation during cancer chemotherapy. Journal of Nutrition & Intermediary Metabolism, vol. 5, Elsevier Inc., pp. 107-116.
Murphy R.A., et al., "Supplementation with Fish Oil Increases First-Line Chemotherapy Efficacy in Patients with Advanced Nonsmall Cell Lung Cancer," Cancer, Aug. 15, 2011, vol. 117(16), pp. 3774-3780.
Ramesh G. et al., "Effect of cis-unsaturated fatty acids on Meth-A ascitic tumour cells in vitro and in vivo," Cancer Letters, Jan. 30, 1998;123(2), Elsevier Science Ireland Ltd., pp. 207-214.
The Wayback Machine—https://web.archive.org/web/20130504185439/http://www.chemicalbook.com, accessed Oct. 25, 2021, 2 pages.

*Primary Examiner* — Sun Jae Yoo
(74) *Attorney, Agent, or Firm* — Hylton-Rodic Law PLLC

(57) ABSTRACT

The present invention relates to the enhancement of the efficacy of anticancer agents by a composition comprising an aqueous phase, an oil phase, EPA and DHA for use in the treatment of solid tumors, wherein EPA and DHA are present in an amount of at least 65% based on the total weight of the oil phase wherein the composition comprises EPA and DHA in a weight ratio between 1:2 and 1:4, or wherein the composition comprises EPA and DHA in a weight ratio between 6:1 and 4:1 and wherein the treatment comprises administering the composition and administering at least one anticancer agent.

16 Claims, No Drawings

COMPOSITION COMPRISING EPA AND DHA FOR AN ENHANCED EFFICACY OF ANTICANCER AGENTS

CROSS REFERENCE TO RELATED APPLICATIONS

This application is a U.S. national stage application of International Application No. PCT/EP2017/075352, Oct. 5, 2017, which claims the benefit of the filing date of European Application 16193256.1, filed Oct. 11, 2016, the contents of which are hereby incorporated by reference in their entirety.

The present invention relates to a composition comprising an aqueous phase, an oil phase, EPA and DHA that enhances the efficacy of an anticancer agent, particularly in the treatment of solid tumors.

One of the best known treatments for cancer is chemotherapy. It generally involves the use of one or more anticancer agents, usually as part of a standardized chemotherapy regimen. Independent of the specific type of chemotherapy, e.g. inhibition of mitosis, hormonal therapy or targeted therapy, the anticancer agents are usually administered systemically to the patient and oftentimes come with severe side effects. This holds particularly true for rather non-specific anticancer agents which are cyto-toxic and interfere with cell division as not only the cancer cells are damaged and/or stressed by said agents. The most common side effects, next to general discomfort, e.g. due to nausea and/or weakness, of chemotherapy include myelosuppression (and consequently also immunosuppression), mucositis and alopecia.

While the systemic administration of the anticancer agents allows for the treatment of most anatomic locations in the body of the patient it needs to be carried out at quite high doses in order to ensure that a sufficient amount of anticancer agents reaches the cancer cells. Disadvantageously, however, such high doses lead to the above-mentioned severe side effects of the anticancer agents. Additionally, the calculation of the doses to be administered is usually just a rough estimate, e.g. calculated based on the weight of the patient. Apparently, such a regimen may additionally aggravate the side effects. The amelioration of these side effects by administration of various compounds, such as compounds comprising EPA and DHA, has been described in the art. Such compositions, however, only treat the symptoms arising from the administration of a given amount of cytotoxic anticancer agents.

US 2003/0068385 A1 describes formulations comprising n-3 fatty acids derived from fish oil. XP-002767899 describes the use of fish oil during chemotherapy. XP-027178516 describes the effects of fish oil containing lipid emulsions in combination with 5-fluorouracil. WO 2012/028543 A1 describes compositions comprising DHA and EPA for administration prior to commencement of chemotherapy. XP-002767900 describes colon cancer cell chemosensation by fish oil emulsions. XP-028586045 describes the antiproliferative and apoptotic effect of n-3 polyunsaturated fatty acidson human colorectal cancer stem-like cells in vitro.

Still, there is the need to improve chemotherapy.

SUMMARY OF THE INVENTION

Surprisingly, it was found that EPA and DHA in certain ratios enhance the efficacy of anticancer agents thus allowing for the administration of a decreased amount of said anticancer agents. Consequently and advantageously, the side effects associated with the administration of anticancer agents are reduced or even prevented already in their origin.

The present invention relates to a composition comprising an aqueous phase, an oil phase, EPA and DHA for use in the treatment of solid tumors wherein EPA and DHA are present in an amount of at least 65% based on the total weight of the oil phase and wherein the treatment comprises parenterally administering the liquid composition and administering at least one anticancer agent. The present invention furthermore relates to a composition comprising an aqueous phase, an oil phase, EPA and DHA and a suboptimal amount of at least one anticancer agent as a medicament.

DETAILED DESCRIPTION

In a first aspect, the invention relates to a composition comprising an aqueous phase, an oil phase, EPA and DHA for use in the treatment of solid tumors wherein EPA and DHA are present in an amount of at least 65% based on the total weight of the oil phase and wherein the treatment comprises parenterally administering the liquid composition and administering at least one anticancer agent.

The term "treatment" or "treating" as used herein in the context of treating a disease pertains generally to treatment and therapy of a patient in which some desired therapeutic effect is achieved, for example the inhibition of the progress of a symptom associated with a disease, such as cancer, and includes a reduction in the rate of progress, a halt in the rate of progress, amelioration of the symptom, and cure of the symptom. Treatment as a prophylactic measure (i.e. prophylaxis) is also included.

Preferably, the composition according to the present invention is a liquid composition. Also preferably, the composition is a composition for parenteral administration.

In a further preferred embodiment the treatment comprises parenterally administering the liquid composition according to the invention. Even more preferably the treatment comprises administering the liquid composition according to the present invention and simultaneously administering at least one anticancer agent.

Oil in Water Emulsion

The composition according to the present invention and the composition obtained or obtainable by the method according to the present invention comprises an aqueous phase and 5 to 30% by weight of an oil phase. Preferably, the composition comprises 5 to 25% by weight of an oil phase, more preferably 5 to 20% by weight of an oil phase, more preferably 5 to 15% by weight of an oil phase, more preferably 5 to 10% by weight of an oil phase, more preferably around 9 to 10% by weight of an oil phase.

The aqueous phase preferably comprises water in a purity suitable for intravenous administration. The amount of water is preferably in the range of from 95 to 70% by weight, preferably 95 to 75% by weight, more preferably 95 to 80% by weight, more preferably 90 to 80% by weight.

Preferably, the composition according to the invention is an emulsion, in particular an oil-in-water emulsion. In case the emulsion is an oil-in-water emulsion, the oil droplets preferably have a mean droplet size ($D_{4,3}$) in the range of from 0.1 µm to 0.3 µm, preferably of from 0.15 µm to 0.25 µm, measured with an LS 13 320 Laser Diffraction Particle Size Analyser (Beckman Coulter) according to USP <729>.

DHA and EPA

The composition according to the present invention comprises omega-3 fatty acids selected from the group consisting of eicosapentaenoic acid (EPA), docosahexaenoic acid (DHA) and mixtures thereof. Preferably, EPA and DHA are present in form of triglycerides. In the following, a reference to "EPA" or "DHA", preferably is a reference to EPA and DHA triglycerides. Even more preferably, EPA and DHA are comprised by the oil phase of the composition.

The term "eicosapentaenoic acid triglycerides" as used herein refers to triglycerides of (5Z, 8Z,11Z,14Z,17Z)-5,8,11,14,17-icosapentaenoic acid, also known as 20:5(n-3). EPA is a an omega-3 fatty acid with a 20-carbon chain and five cis double bonds; the first double bond is located at the third carbon from the omega end. The term "docosahexaenoic acid triglycerides" as used herein refers to triglycerides of all-cis-docosa-4,7, 10, 13, 16, 19-hexa-enoic acid, also known as is 22:6(n-3). DHA is an omega-3 fatty acid that is a primary structural component of the human brain, cerebral cortex, skin, sperm, testicles and retina. Docosahexaenoic acid is a 22-carbon chain with six cis double bonds, the first double bond being located at the third carbon from the omega end. EPA and DHA triglycerides may be obtained by any way known to those skilled in the art.

It is known that DHA and EPA and the derivatives thereof are contained per se, or in the form of glycerides and in the form of other derivatives, in natural fats and oils, particularly in fats and oils of aquatic animals (e.g., fish, marine mammals, and crustaceans such as krill and other euphausiids), animal tissues (e.g., brain, liver, eyes, etc.) and animal products such as eggs or milk. Thus, for example, they may be extracted from animal sources including aquatic animals (e.g., fish, marine mammals, and crustaceans such as krill and other euphausiids), animal tissues (e.g., brain, liver, eyes, etc.) and/or animal products such as eggs or milk.

Some methods for the isolation of these docosahexaenoic acid (DHA) and eicosapentaenoic acid (EPA) and their derivatives and their conversion to pure docosahexaenoic acid (DHA) triglycerides and eicosapentaenoic acid (EPA) triglycerides are described in the art. Such isolation by purification can be achieved by any means known to those of skill in the art and can include the extraction, e.g. by supercritical fluid extraction, of an oil from an organism which produces DHA and/or EPA and the subsequent purification via chromatographic methods. Alternatively, the oils can be extracted using extraction techniques such as are described in U.S. Pat. No. 6,750,048. Additional extraction and/or purification techniques are taught e.g. in WO2001076715 and WO/2001/076385.

EPA and DHA are present in an amount of at least 65% based on the total weight of the oil phase. In other words, at least 65% by weight of the oil phase, such as from 65% by weight to 95% by weight of the oil phase, more preferably at least 70% by weight of the oil phase, more preferably at least 75% by weight of the oil phase, more preferably at least 80% by weight of the oil phase, more preferably of from 85 to 90% by weight of the oil phase, present in the composition according to the invention or in the composition obtained or obtainable by the method as described above consists of eicosapentaenoic acid triglyceride, docosahexaenoic acid triglyceride or a mixture thereof.

Preferably, the oil phase comprises a mixture of EPA triglycerides and DHA triglycerides, wherein the weight ratio of EPA triglycerides relative to all DHA triglycerides is in the range of from 1:5 to 7:1, such as 1:5, 1:4, 1:3, 1:2, 1:1, 2:1, 3:1, 4:1, 5:1, 6:1 or 7:1. More preferably, the composition comprises EPA and DHA in a weight ratio between 1:2 and 1:4 or between 6:1 and 4:1. Even more preferably the composition comprises EPA and DHA in a weight ratio between 6:1 and 4.5:1. It was surprisingly found that EPA and DHA in these ratios enhance the efficacy of anticancer agents thus advantageously allowing for the administration of a decreased amount of said anticancer agents.

Medium Chain Fatty Acid Derivatives

Preferably, the oil phase present in the composition comprises less than 1% by weight, more preferably less than 0.5% by weight, more preferably less than 0.1% by weight, more preferably less than 0.05% by weight, more preferably less than 0.01% by weight, more preferably essentially no, more preferably no, medium chain fatty acid derivatives, wherein this amount refers to the sum of all medium chain fatty acid derivatives present and is based on the total weight of the oil phase. The term "essentially no" in this context refers to an amount<0.01% by weight including 0% by weight.

The term "medium chain fatty acid derivative" as used hereinunder and above refers to fatty acid derivatives, such as mono-, di- or triglycerides (MCT), comprising a medium chain fatty acid or alkyl esters of medium chain fatty acids these fatty acids being 6 to 12 carbon atoms in length. Medium chain fatty acids include but are not limited to caproic acid, caprylic acid, capric acid and lauric acid.

Surprisingly, it has been found that stable compositions may be provided without these medium chain fatty acid derivatives which, due to the fact that MCTs may be omitted, may comprise an even higher amount of EPA derivatives and DHA derivatives. This finding is particularly surprising since the prior art emphasizes that omega-3 fatty acid comprising compositions should contain MCTs to enhance their stability.

Surfactant

The composition of the present invention preferably comprises at least one amphoteric surfactant. The term "surfactant" as used within the meaning of the present invention refers to compounds which stabilize the composition by reducing the interfacial tension between the oil phase and the water phase and which typically comprise at least one hydrophobic group (their tail) and at least one hydrophilic group (their head). These surfactants (which may also be referred to as emulsifiers) are preferably used in amounts effective to provide, optionally together with further surfactants present, stable and even distribution of the oil phase within the aqueous phase. In particular, these surfactants are selected from surfactants which have been approved for parenteral administration. The term "amphoteric surfactant" refers to surfactants which carry a charge that varies depending on the pH of the solution. At low pH (acidic conditions), they act as cationic surfactants while at high pH (basic), they act as anionic surfactants. When both charge groups are permanent, the surfactants are sometimes also called zwitterionic.

Preferably, the at least one amphoteric surfactant is lecithin. Within the meaning of the present invention the term "lecithin" refers to a naturally occurring or synthetic lecithin that may be suitably refined. Suitable lecithins include, but are not limited to, lecithins derived from egg, corn or soybean or mixtures thereof. Further suitable lecithins include, but are not limited to, dihexanoyl-L-alpha-lecithin, dioctanoyl-L-alpha-lecithin, didecanoyl-L-alpha-lecithin, didodecanoyl-L-alpha-lecithin, ditetradecanoyl-L-alpha-lecithin, dihexadecanoyl-L-alpha-lecithin, dioctadecanoyl-L-alpha-lecithin, dioleoyl-L-alpha-lecithin, dilinoleoyl-L-alpha-lecithin and alpha-palmitol. Lecithins are typically mixtures of diglycerides of fatty acids linked to the choline ester of phosphoric acid and can contain differing amounts of other compounds depending on the method of isolation. Typically, commercial lecithin is a mixture of acetone-insoluble phosphatides. Preferably, the lecithin is obtained from egg or from seeds including soybean and corn, using methods well known in the art. Lecithin obtained from soybean is referred to herein as soy lecithin. Lecithin obtained from egg is referred to herein as egg lecithin.

Preferably, the composition comprises lecithin as amphoteric surfactant, more preferably the lecithin is selected from the group consisting of egg lecithin, soy lecithin, and mixtures thereof.

As to the soy lecithin, said soy lecithin typically comprises at least 50% by weight of phospholipids, more preferably of from 50 to 95% by weight, more preferably of from 70 to 80% by weight and most preferably of from 75 to 85% by weight, based on the total weight of the soy lecithin. The soy lecithin, as described above, usually comprises at least phosphatidylcholine and phosphatidylethanolethanolamine, and usually further comprises phosphatidylinositol and phosphatidic acid. A typical composition comprises phosphatidylcholine in an amount in the range of from 70% by weight to 80% by weight and phosphatidylethanolethanolamine in an amount in the range of from 5 to 10% by weight, based on the total weight of the soy lecithin. Such soy lecithin is commercially available, for example as Epikurin™ 170.

As to the egg lecithin, said egg lecithin typically comprises at least 50% by weight of phospholipids, preferably at least 80% by weight, more preferably at least 90% by weight, based on the total weight of the egg lecithin. The egg lecithin, as described above, usually also comprises phosphatidylcholine, phosphatidylethanolethanolamine, phosphatidylinositol and phosphatidic acid. A typical composition comprises phosphatidylcholine in an amount in the range of from 60 to 85% by weight and phosphatidylethanolethanolamine in an amount in the range of from 7 to 18% by weight, based on the total weight of the egg lecithin. Such egg lecithins are commercially available, for example as PL 90 or Lipoid E80. It is to be understood that lecithin may be employed in combination with other amphoteric surfactants. Preferably, the composition only comprises lecithin as amphoteric surfactant.

The total amount of amphoteric surfactants within the composition, more preferably of lecithin, is preferably in the range of from 0.5 to 5% by weight, more preferably 0.75 to 3% by weight, more preferably in the range of from 1% by weight to 2% by weight, such as 1.0, 1.1, 1.2, 1.3, 1.4, 1.5, 1.6, 1.7, 1.8, 1.9 or 2.0% by weight, based on the total weight of the composition.

Co-Solvent

The composition preferably further comprises at least one co-solvent. The term co-solvent refers to molecules that may increase the stability of the composition according to the invention. In addition to making the environment more hydrophobic by reducing the dielectric constant of water, co-solvents increase the amount of molecularly dispersed surfactant in the aqueous phase. Availability of free surfactant aids in the solubilisation of hydrophobic molecules by creating pockets of hydrophobic regions within the aqueous phase. Examples of co-solvents include ethanol, glycerin, propylene glycol and polyethylene glycol (PEG).

Preferably, the at least one co-solvent is a polyalkylene glycol or an alkylene glycol, preferably polyethylene glycol or propylene glycol, more preferably polyethylene glycol.

Co-Surfactant

The composition preferably comprises at least one co-surfactant. A co-surfactant is an amphiphilic molecule, i.e. a molecule that contains both hydrophilic and lipophilic groups. Usually a co-surfactant substantially accumulates with the surfactant at the interfacial layer.

The hydrophile-lipophile balance (HLB) number is used as a measure of the ratio of hydrophilic and lipophilic groups present in a surfactant or co-surfactant, respectively. Usually a co-surfactant with a very low HLB value (thus with a relatively high affinity to oil) is used together with a surfactant with a high HLB to modify the overall HLB of the system. Unlike surfactant, the co-surfactant may not be capable of forming self-associated structures, like micelles, on its own. Several kinds of molecules including nonionic surfactants, alcohols, amines and acids, can function as co-surfactants in a given system. The quantity of a co-surfactant in a system is usually less than that of the surfactant and it often serves to modify the overall HLB value of the system. The co-surfactant has the effect of further reducing the interfacial tension, whilst increasing the fluidity of the interface. Co-surfactants may also adjust the curvature of the interfacial film by partitioning between the tails of the surfactant chains, allowing greater penetration of the oil between the surfactant tails.

Preferably, the at least one co-surfactant is an unsaturated fatty acid, preferably an omega-9 fatty acid, more preferably a monounsaturated omega-9 fatty acid, more preferably oleic acid. Surprisingly, it has been found that emulsions comprising oleic acid in combination with a co-solvent and an amphoteric surfactant are particularly stable.

The total amount of at least one co-surfactant is preferably in the range of from 0.01 to 1% by weight, more preferably in the range of from 0.02% by weight to 0.5% by weight, more preferably in the range of from 0.03% by weight to 0.25% by weight, based on the total weight of the composition. Preferably, the composition comprises less than 0.03% by weight of sodium oleate based on the total weight of the composition. More preferably, the composition comprises less than 0.02% by weight, even more preferably less than 0.01% by weight sodium oleate.

Preferably, the composition as described above comprises oleic acid as co-surfactant, lecithin as amphoteric surfactant and polyethyleneglycol and/or propylene glycol as co-solvent(s). It is to be understood that polyethylene glycol may be employed in combination with other co-solvents such as any one of the co-solvents mentioned above. Preferably, the composition only comprises polyethylene glycol and/or propylene glycol as co-solvent.

In case polyethylene glycol is employed as co-solvent, the polyethylene glycol preferably has a mean molecular weight in the range of from 100 to 20000 Da, more preferably in the range of from 200 to 1000 Da, more preferably in the range of from 300 to 600 Da, most preferably around 400 Da.

Preferably, the co-solvent is selected from the group consisting of PEG 200, PEG 300, PEG 400, PEG 600, PEG 1000, PEG 1450, PEG 3350, PEG 4000, PEG 6000, PEG 8000 and PEG 20000. Most preferably, the co-solvent is PEG 400.

Preferably, the total amount of co-solvents present ranges from 0.1 to 2.0% by weight, more preferably from 0.25 to 1.75% by weight, more preferably from 0.50 to 1.50% by weight, more preferably from 0.70 to 1.40% by weight, more preferably from 0.80 to 1.30% by weight, and even more preferably from 0.90 to 1.20% by weight, based on the total weight of the composition.

Surprisingly, it has been found that emulsions comprising polyethylene glycol and/or propylene glycol as well as lecithin are particularly stable.

Other Surfactants

It is noted that the composition as described above may comprise any other suitable surfactant or any other co-surfactant provided that the composition comprises less than 0.03% by weight of sodium oleate based on the total weight of the composition. As suitable other surfactants, e.g. nonionic or anionic surfactants may be mentioned. Thus, also in the method described above, any other surfactant such as e.g. nonionic or anionic surfactants may be added, such as in particular in step (a), provided that less than 0.03% by weight of sodium oleate based on the total weight of the final composition are added during the method.

Preferably, the composition comprises less than 0.02% by weight, more preferably less than 0.01% by weight, more preferably essentially no sodium oleate, preferably no sodium oleate. The term "essentially no" is denoted to mean that essentially no, that is an amount of <0.01% by weight including 0% by weight, sodium oleate, preferably 0% by weight, is added to the composition during the preparation process. It is noted that in case oleic acid is added to the mixture during the preparation of the composition, and in case any further sodium salts, such as sodium hydroxide, are added during the preparation process, it may not be ruled out that at least a portion of this oleic acid is being transformed into its corresponding sodium salt, i.e. into sodium oleate, even though it is contemplated that substantially all of the oleic acid should be present in the oil phase and that should thus not be transformed to the corresponding sodium salt. Such minor amount of sodium oleate which may be formed is thus included in term "essentially no".

Tonicity Agent

Preferably, the composition according to the invention comprises at least one tonicity agent. Tonicity agents are substances which are used to confer tonicity to e.g. pharmaceutical compositions. A tonicity agent useful in the present composition can be any pharmaceutically acceptable tonicity agent. Common tonicity agents include, but are not limited to, agents selected from the group consisting of sodium chloride, mannitol, lactose, dextrose (hydrous or anhydrous), sucrose, glycerol, and sorbitol, and solutions of the foregoing. Thus, according to a preferred embodiment of the invention, the present invention also relates to a composition, as described above, as well as to a composition obtained or obtainable by the method according to the invention, wherein the composition comprises at least one tonicity agent. Preferably, the tonicity agent is glycerol.

If present, preferably the total amount of tonicity agents present is in the range of 0 to 10% by weight, more preferably from 1 to 5% by weight, more preferably from 1 to 4% by weight, more preferably from 1 to 3% by weight, more preferably from 1.5 to 2.8% by weight, and even more preferably from 2.0 to 2.5% by weight, based on the total weight of the composition.

Preferably, the composition has an osmolality in the range 305 to 420 mOsmol/kg, more preferably in the range of from 300 to 420 mOsmol/kg, measured with a Vapor Pressure Osmometer, Model 5520 (Vapro™) according to USP <785>.

Antioxidant

Preferably, the composition according to the invention comprises at least one antioxidant, i.e., an agent with antioxidant activity, preferably at least two agents with antioxidant activity.

An antioxidant useful in the present composition can be any pharmaceutically acceptable compound having antioxidant activity including sodium metabisulfite, sodium bisulfite, sodium sulfite, sodium thiosulfate, sodium formaldehyde sulfoxylate, sodium formaldehyde bisulfite, thioglycerol, thiosorbitol, thioglycolic acid, cysteine hydrochloride, n-acetyl-cysteine, citric acid, alpha-tocopherol, beta-tocopherol, gamma-tocopherol, Trolox (soluble form of vitamin E), butylated hydroxyanisole (BHA), butylated hydroxytoluene (BHT), t-butylhydroquinone (TBHQ), monothioglycerol, propyl gallate, lopurinol, carnosine, histidine, enzymes, such as superoxide dismutase, catalase, selenium glutathione peroxidase, phospholipid hydroperoxide and glutathione peroxidase, Coenzyme Q 10, tocotrienols, carotenoids, quinones, bioflavonoids, polyphenols, bilirubin, ascorbic acid, isoascorbic acid, uric acid, metal-binding proteins, ascorbic acid palmitate, an antioxidant obtained or obtainable from rosemary and rosemary extract.

The at least one agent with antioxidant activity preferably is tocopherol, even more preferably it is selected from the group consisting of alpha-tocopherol, beta-tocopherol, gamma-tocopherol, ascorbic acid, and mixtures of two or more thereof.

If present, the total amount of agents with antioxidant activity is preferably in the range of from 0.01 to 0.05% by weight, more preferably from 0.01 to 0.04% by weight, more preferably from 0.01 to 0.03% by weight, and even more preferably from 0.015 to 0.025 by weight, based on the total weight of the composition.

More preferably, the composition comprises at least two different agents with antioxidant activity. For example, the present invention comprises alpha-tocopherol and beta-tocopherol, or alpha-tocopherol and gamma-tocopherol, or beta-tocopherol and gamma-tocopherol, or alpha-tocopherol and ascorbic acid, or beta-tocopherol and ascorbic acid, or gamma-tocopherol and ascorbic acid. According to a further preferred embodiment, the present invention comprises a mixture of beta-tocopherol, alpha-tocopherol and gamma-tocopherol.

Further Additives

It is to be understood that other physiologically safe additives may also be present in the composition according to the invention including, but not limited to, salts commonly used for intravenous application such as sodium chloride and nonelectrolytes such as glucose, pH modifiers (such as acetic acid and sodium acetate) and buffers (such as acetate, lactate, and phosphate buffer systems composed of the acid and a salt of the acid) as well as selenium compounds.

One skilled in the art will understand that the pH of the composition may for example be adjusted through the use of buffers, such as phosphate buffers, or neutralization agents, such as sodium hydroxide. Preferably, the composition according to the present invention has a pH value close to physiological pH or above since it is contemplated that at such pH values the fatty acids are less prone to peroxidation. The final pH of the composition is preferably in the range of from 7.0 to 10, preferably in the range of from 8 to 10.

By way of example, the composition may further comprise other additives conventionally used in pharmaceutical compositions. Such additives include carbohydrate nutrients, electrolytes, amino acids, vitamins, trace minerals, preservatives, anti-foaming agents, buffering agents, chelating agents, and mixtures thereof. The amounts of such additives can be readily determined by one skilled in the art according to the particular properties desired.

The components of the composition according to the present invention described above can be combined freely as long as no apparent inconsistencies result. Especially preferred embodiments of the composition according to the invention are still explicitly described in the following.

The composition according to the invention preferably further comprises at least one amphoteric surfactant, at least one co-surfactant and at least one co-solvent, wherein at least one co-surfactant is oleic acid, and wherein the composition comprises less than 0.03%, more preferably less than 0.01% by weight of sodium oleate based on the total weight of the composition.

The composition according to the present invention more preferably further comprises at least one amphoteric surfactant, at least one co-surfactant and at least one co-solvent, wherein the composition comprises less than 0.03% by weight of sodium oleate, based on the total weight of the composition, and wherein the at least one co-solvent is a polyalkylene glycol or an alkylene glycol, preferably polyethylene glycol or propylene glycol, more preferably polyethylene glycol.

The composition according to the present invention more preferably further comprises at least one amphoteric surfactant, at least one co-surfactant and at least one co-solvent, wherein the at least amphoteric surfactant is lecithin, and wherein the co-solvent is polyethylene glycol and/or propylene glycol, and wherein the composition comprises less than 0.03% by weight of sodium oleate based on the total weight of the composition.

Anticancer Agents

The composition according to the present invention can be used together with any suitable anticancer agent. Various anticancer agents are known and readily available to the skilled person.

In a preferred embodiment, the at least one anticancer agent comprises a kinase inhibitor, a receptor tyrosine kinase inhibitor, an alkylating agent, an antimetabolite, a topoisomerase inhibitor, a cytostatic antibiotic, a DNA intercalator, a mitosis inhibitor, a hormone, a hormone receptor agonist, a hormone antagonist, a radioactive agent, a photodynamic agent, an immunomodulator, a proteasome inhibitor, an antibody or an agent selected from the group consisting of arsen trioxide, asparaginase, hydroxycarbamide, miltefosin, tretinoin, alitretinoin, bexaroten, thalidomide, lenalidomide and mifamurtide.

More preferably, the at least one anticancer agent comprises a kinase inhibitor, an antimetabolite, an alkylating agent, a topoisomerase inhibitor, a mitosis inhibitor, a cytostatic antibiotic and/or a DNA intercalator, a hormone antagonist or an antibody.

A kinase inhibitor, also known as protein kinase inhibitor, preferably is an enzyme inhibitor that blocks the action of at least one protein kinase which adds a phosphate group to a protein. Protein kinase inhibitors can be used to treat diseases mediated by hyperactive protein kinases (including mutant or overexpressed kinases in cancer). More preferably, the kinase inhibitor is selected from the group consisting of sunitinib, sorafenib, imatinib, dasatinib, erlotinib, gefitinib, lapatinib, ibrutinib, vemurafenib, afatinib, axitinib, bosutinib, cabozantinib, crizotinib, nilotinib, pazopanib, pegabtanib, ponatinib, regorafenib, bosutinib, trametinib and temsirolimus.

An antimetabolite according to the present invention is any suitable agent that inhibits the use of a metabolite, which is another chemical that is part of normal metabolism. The antimetabolite is preferably cytotoxic, even more preferably it inhibits cell growth and/or cell division. More preferably, the antimetabolite is selected from the group consisting of methotrexate, pralatrexate, pemetrexed, cladribine, fludarabine, nelarabine, mercaptopurine, tioguanine, pentostatine, fluoruracil, tegafur, capecitabine, cytarabine, decitabine, azacytidine, floxuridine and gemcitabine.

The alkylating agent according to the present invention can be any suitably alkylating agent. Preferably, the alkylating agent is an alkylating antineoplastic agent and attaches an alkyl group to DNA. More preferably, the alkyl group is attached to the guanine base of DNA at the number 7 nitrogen atom of the purine ring. In a more preferred embodiment according to the invention the alkylating agent is selected from the group consisting of cyclophosphamide, ifosfamide, trofosfamide, melphalan, chlorambuci, thiotepa, busulfane, treosulfane, bendamustine, carmustine, lomustine, nimustine, cisplatin, carboplatin, oxaliplatin, streptozotocin, procarbazine, dacarbazine, trabectedine and temozolomide.

The topoisomerase inhibitor according to the invention can be any suitable topoisomerase inhibitor. Preferably, the topoisomerase inhibitor inhibits the action of a topoisomerase enzyme, more preferable topoisomerase I and/or II. More preferably, the topoisomerase inhibitor blocks the ligation step of the cell cycle and/or induces apoptosis. In a more preferred embodiment according to the invention the topoisomerase inhibitor is selected from the group consisting of topotecan, irinotecan, teniposide, HU-331, etoposide and etoposide phosphate.

The mitosis inhibitor according to the present invention can be any suitable agent that inhibits mitosis. Preferably, the mitosis inhibitor disrupts microtubules and/or microtubule polymerization during cell division. The mitosis inhibitor is preferably derived from a plant alkaloid. In a more preferred embodiment the mitosis inhibitor is selected from the group consisting of vincristine, vinblastine, vindesine, vinorelbine, vinflunin, eribulin, estramustine, ixabepilone, cabacitaxel, paclitaxel and docetaxel.

The cytostatic antibiotic and/or DNA intercalator according to the invention may be any suitable cytostatic antibiotic and/or DNA intercalator known to the skilled person. Preferably the cytotstatic antibiotic cytostatic antibiotic and/or DNA intercalator interrupts cell division, intercalates into DNA, generates highly reactive free radicals that damage intercellular molecules and/or inhibits the topoisomerase. In a more preferred embodiment the cytostatic antibiotic and/or DNA intercalator is selected from the group consisting of anthracyclines and bleomycins. In an even more preferred embodiment the cytostatic antibiotic and/or DNA intercalator is selected from the group consisting of dactinomycine, dexrazosan, daunorubicine, idarubicine, doxorubicine, epirubicine, mitoxantrone, amsacrine, bleomycine and mitomycine.

A hormone antagonist according to the invention may be any agent that antagonizes hormone-mediated effects, e.g. it may be a hormone receptor antagonist. The hormone receptor is preferably located on the cell surface of the cancer cell or it is located intracellularly. More preferably, the hormone receptor is a receptor for peptide hormones, glycoprotein hormones or steroid hormones. In a further preferred embodiment the hormone antagonist is an antagonist of the estrogen or androgen receptor. The hormone antagonist may also be an enzyme inhibitor preventing the formation of functional hormones in the body. In a more preferred embodiment the hormone antagonist is selected from the group consisting of anastrozole, letrozole, exemestane, tamoxifen, toremifene, fulvestrant, abarelix, degarelix, cyproterone acetate, nilutamide, bicalutamide and flutamide.

A hormone agonist according to the invention may be any agent that conveys hormone effects, e.g. it may be an agonist acting upon a hormone receptor. More preferably the hormone agonist has a growth-inhibiting and/or cytotoxic effect on tumor cells. In preferred embodiments the hormone agonist is selected from the group consisting of progestogens, androgens, estrogens and somatostatin analogs. In a more preferred embodiment the hormone agonist is selected from the group consisting of tamoxifen, medroxyprogesteron, megestrol, estramustin, buserelin, goserelin, leuprorelin, triptorelin and histrelin.

The antibody may be any antibody suitable as an anticancer agent. Preferably, the antibody is a monoclonal antibody, an antibody labelled with a radioactive compound and/or an antibody conjugated to a cytotoxic drug or prodrug. More preferably, the antibody makes a cancer cell more visible to the immune system of the patient, the antibody blocks the growth of the cancer cell, preferably by blocking of a growth factor receptor, the antibody inhibits or prevents angiogenesis, the antibody delivers radiation to a cancer, the antibody delivers a cytotoxic drug or prodrug to the cancer cell and/or the antibody is ingested by the cancer cell. In a more preferred embodiment the antibody is selected from the group consisting of bevacizumab, panitumumab, cetuximab, trastuzumab, ipilimumab, catumaxomab, ramucirumab, ertumaxomab, abituzumab, amatuximab, anetumab ravtansine, atezolizumab, codrituzumab, demcizumab, durvalumab, emibetuzumab, ensituximab, imalumab, indusatumab vedotin, lifastuzumab vedotin, lorvotuzumab mertansine, lumretuzumab, margetuximab, mirvetuximab, nivolumab, olaratumab, onutuximab, oportuzumab, patritumab, pemtumomab, pertuzumab, racotumomab, sacituzumab govitecan, seribantumab, tigatuzumab, tremelimumab, vanicizumab, dalotuzumab, ficlatuzumab, icrucumab, pembrolizumab and bavituximab.

Even more preferably, the treatment is a combination therapy and most preferably comprises the administration of at least two, two, at least three, three or four different anticancer agents. Preferably, the at least two different anticancer agents disrupt different stages of the cell cycle and/or act on different molecule classes of the cancer cell, more preferably nucleic acid, such as DNA or RNA, and protein, such as enzymes or receptors.

Preferably, where the solid tumor to be treated is colorectal cancer, more preferred colon carcinoma the at least one anticancer agent is selected from the group consisting of 5-FU, Irinotecan, Leucovorin, Oxaliplatin, Capecitabin, Cetuximab, Panitumomab, Regorafenib, Aflibercept, and Bevacizumab. More preferably, the at least one anticancer agent is a combination of the three anticancer agents folinic acid, 5-FU and Oxaliplatin or a combination of the three anticancer agents folinic acid, 5-FU and Irinotecan. Most preferably, the at least one anticancer agent is a combination of four anticancer agents consisting of either of the two combinations of three anticancer agents mentioned above additionally combined with either Regorafenib or an antibody selected from the group consisting of Cetuximab, Panitumomab and Bevacizumab.

Preferably, where the solid tumor to be treated is breast cancer the at least one anticancer agent is selected from the group consisting of Bevacizumab, an anthracycline, preferably Doxorubicin, Epirubicin, a Taxane, preferably Docetaxel, Paclitaxel, Vinorelbin and Eribulin.

More preferably, where the solid tumor to be treated is breast cancer the at least one anticancer agent is one of the following combinations: Docetaxel and Doxorubicin; Capecitabin and Paclitaxel; Gemcitabin and Paclitaxel; Docetaxel and Capecitabin; Doxorubicin and Cyclophosphamid; Epirubicin and Cyclophosphamid; Paclitaxel and Trastuzumab; Paclitaxel and Bevacizumab; Bevacizumab and Capecitabin; or Gemcitabin and Carboplatin. Even more preferably, the at least one anticancer agent is a combination of the following three anticancer agents: 5-FU, Doxorubicin and Cyclophosphamid; Cyclophosphamid, Methotrexat and 5-FU; or Cyclophosphamid and Epirubicin and Paclitaxel.

Preferably, where the solid tumor to be treated is an estrogen receptor positive breast cancer the at least one anticancer agent comprises an anticancer agent suitable for an anti-estrogen therapy. More preferably the at least one anticancer agent comprises a combination of two anticancer agents selected from Tamoxifen and an aromatase inhibitor; Tamoxifen and Fulvestrant; or Tamoxifen and an GNRH-analog, even more preferably a combination of three anticancer agents selected from Tamoxifen, an aromatase inhibitor and an GNRH-analog; or Tamoxifen, Fulvestrant and an GNRH-analogue.

Preferably, where the solid tumor to be treated is HER2 positive breast cancer the at least one anti-cancer agent comprises an anticancer agent suitable for an anti-HER2 therapy, preferably Trastuzumab. More preferably, where the solid tumor is an HER2 positive tumor the at least one anticancer agent comprises one of the following combinations: Tamoxifen and an aromatase inhibitor; Tamoxifen and Fulvestrant; or Tamoxifen and an GNRH-analog. Even more preferred is one of the following combinations: Tamoxifen, an aromatase inhibitor and an GNRH-analog; or Tamoxifen, Fulvestrant and an GNRH-analog.

Administration of the Composition

As disclosed above, the administration of a composition according to the present invention advantageously enhances the efficacy of an anticancer agent rather than merely reduces and/or ameliorates side effects of such an anticancer agent. In a preferred embodiment the composition according to the invention therefore enhances the efficacy of the at least one anticancer agent that is administered in the treatment of solid tumors, allowing for a reduction of the dose of the at least one anticancer agent as compared to the standard dose of that agent.

The term "standard dose" refers to the amount of anticancer agent which is to be administered to the patient not taking into account the enhanced efficacy of the anticancer agent brought about by the composition according to the invention. In other words, the term "standard dose" refers to the amount of anticancer agent which would be prescribed to a patient in need thereof if the present and inventive compositions were not available and/or in a treatment wherein the treatment comprises administering the at least one anticancer agent without administering the composition according to the present invention. Exemplarily and preferably the dose may be given in g, mg or ml of the at least one anticancer agent to be administered to the patient. The standard dose may preferably be in relation to the body weight of the patient to be treated, preferably in g/kg, mg/kg or ml/kg of the. The dose may furthermore preferably be a daily dose to be administered in a specified time interval, e.g. g/h, mg/h or ml/h. Also preferred, the dose may be a dose given in relation to the body weight of the patient to be treated and in relation to a specified time interval, e.g. g/kg/h, mg/kg/h or ml/kg/h. More preferably the dose is a daily dose, preferably a daily dose calculated for a specific patient to be treated.

In a preferred embodiment the at least one anticancer agent is administered at a dose below the standard dose of said anticancer agent. More preferably, the at least one anticancer agent is administered at a dose of 20 to 90%, even more preferably 30 to 80% or 30 to 70% and most preferably 40 to 70% of the standard dose of said at least one anticancer agent. In case the at least one anticancer agent is not a single anticancer agent the dose standard dose preferably is calculated as the sum of the more than one anticancer agents.

Surprisingly, it was found that already a dose of 0.1 ml of the composition of present invention per kg body weight of a patient was sufficient to mediate the inventive enhancement of the efficacy of the anticancer agent. Therefore, in a further preferred embodiment the composition of the present invention is administered at a dose of 0.1 and 3.0 ml/kg body weight per day. More preferably, the composition of the present invention is administered at a dose of 0.5 and 2.5 ml/kg body weight per day and most preferably the composition of the present invention is administered at a dose of 1.0 and ≤2.0 ml/kg body weight per day.

The composition of the present invention is preferably used in the treatment of solid tumors wherein the treatment comprises administering the composition and administering at least one anticancer agent. Preferably, the composition and/or the at least one anticancer agent are administered parenterally. The composition of the present invention may be administered simultaneously with, prior to or after the administration of the at least one anticancer agent. Preferably, the composition of the present invention is administered prior to the administration of the at least one anticancer agent. In a further preferred embodiment the composition of the present invention is administered simultaneously with the at least one anticancer agent.

An administration of the composition according to the invention simultaneously with or prior to the administration of the at least one anticancer agent is particularly preferred if the application is carried out by means of injection or infusion.

The tumor to be treated can be any tumor treatable by the at least one anticancer agent administered. Preferably, the tumor is a solid tumor. More preferably it is a solid and malignant tumor. Even more preferably the tumor is a carcinoma or a sarcoma. Most preferably, the tumor is an adenocarcinoma or a squamous cell carcinoma, preferably an adenocarcinoma.

In a further preferred embodiment the solid tumor is selected from the group consisting of colorectal cancer, stomach cancer, breast cancer, lung cancer, mesothelioma, melanoma, oesophagus cancer, biliary cancer, endometrium cancer, cervical cancer, ovarian cancer, pancreatic cancer, prostate cancer, thyroid cancer, skin cancer, liver cancer, bladder cancer, kidney cancer, gastrointestinal stroma tumors (GIST), head and neck cancer, neuroendocrine tumors, osteosarcoma, vaginal cancer, cns tumors, soft tissue sarcoma, and cancer of unknown primary (CUP).

More preferably, the solid tumor is selected from the group consisting of colorectal cancer, breast cancer, lung cancer, ovarian cancer and pancreatic cancer. Even more preferably, the solid tumor is selected from the group consisting of colorectal cancer, breast cancer and pancreatic cancer. Even more preferably, the solid tumor is colorectal cancer or breast cancer. Most preferably the solid tumor is colon cancer.

In a further preferred embodiment the colorectal cancer is selected from the group consisting of colon carcinoma, carcinoma of the small intestine and carcinoma of the rectum. More preferably, the colorectal cancer is colon carcinoma or carcinoma of the small intestine. Most preferably, the colorectal cancer is colon carcinoma.

In a further preferred embodiment the colon carcinoma is selected from the group consisting of adenocarcinoma, carcinoid and sarcoma. Most preferably the colon carcinoma is adenocarcinoma.

In a further preferred embodiment the tumor is located in the colon, more preferably the colon ascendens, the colon transversum, the colon descendens or the colon sigmoideum.

In a further preferred embodiment the solid tumor is breast cancer selected from the group consisting of carcinoma in situ, invasive ductal carcinoma, invasive lobular carcinoma and medular carcinoma. More preferably, the breast cancer is an invasive ductal or lobular carcinoma.

In a further preferred embodiment the breast cancer is hormone receptor positive or hormone receptor negative. In a further preferred embodiment the breast cancer is HER2 positive or HER2 negative.

In a further preferred embodiment the tumor, preferably solid tumor, is in stage I, IIa, IIb, IIc, IIIa, IIIb, IIIc, IVa or IVb, more preferably in stage IIa, IIIa, IVa or IVb.

In a further preferred embodiment the solid tumor is lung cancer selected from the group consisting of small cell lung cancer (SCLC) and non-small cell lung cancer (NSCLC). More preferably, the lung cancer is NSCLC and selected from the group consisting of adenocarcinoma, squamous cell carcinoma and large cell lung carcinoma. More preferably, the NSCLC is an adenocarcinoma or a squamous cell carcinoma. Most preferably, the NSCLC is an adenocarcinoma. In a further preferred embodiment the lung cancer, preferably NSCLC, exhibits an activating EGFR mutation. In a further preferred embodiment the lung cancer, preferably NSCLC, is in stage II, III or IV.

In a further preferred embodiment the solid tumor is ovarian cancer selected from the group consisting of malignant epithelial tumor, malignant germ band and/or stroma tumor, malignant germ cell tumor and borderline tumor. More preferably, the malignant epithelial tumor is selected from the group consisting of serous, endometrioid, clear cell, mucinous, undifferentiated and unclassifiable epithelial ovarian cancer. More preferably, the malignant germ cell tumor is ovarian teratoma, preferably immature teratoma. More preferably, the stroma tumor is a granulosa tumor.

In a further preferred embodiment the solid tumor is pancreatic cancer selected from the group consisting of tumors of the connective tissue, carcinoma of the exocrine pancreas and carcinoma of the endocrine pancreas. More preferably, the exocrine pancreas carcinoma is selected from the group consisting of adenocarcinoma, cystadenocarcinoma and signet ring cell carcinoma. The endocrine pancreas carcinoma is more preferably selected from the group consisting of malignant insulinoma, glucagonoma, gastrinoma, VIPoma and somatostatinoma. The tumors of the pancreatic connective tissue are more preferably selected from the group consisting of sarcoma and lymphoma.

The Method for Preparing the Composition

The present invention also provides a method for preparing the inventive composition. The method comprises:

(a) providing an aqueous phase comprising the at least one co-solvent and the at least one amphoteric surfactant, (b) providing an oil phase comprising omega-3 fatty acid triglycerides selected from the group consisting of eicosapentaenoic acid triglyceride, docosahexaenoic acid triglyceride and mixtures thereof, (c) mixing the oil phase according to (b) with the aqueous phase according to (a), wherein the at least one co-surfactant is added either in step (b) or in step (c), and wherein less than 0.03% by weight of sodium oleate based on the total weight of the final composition are added during the method.

It is to be understood that any one of the optional further components of the composition may be added in any one of steps (a) to (c), or in one or more additional steps.

Step (a)

Step (a) is preferably carried out by mixing the at least one co-solvent and the at least one amphoteric surfactant together or subsequently with water. This step is preferably carried out at a temperature in the range of from 25 to 70°

C., wherein during this step, the temperature may be varied or held essentially constant. Preferably, initially, the at least one co-solvent is mixed with water. Preferably, subsequently, the at least one amphoteric surfactant is added to the mixture comprising water and the at least one co-solvent thereby forming a dispersion. Preferably, the resulting mixture is mixed for example with a high shear mixer. Preferably, the mixture is then heated to a temperature in the range of from 40 to 70° C., preferably, 50 to 65° C., more preferably 55 to 60° C., preferably for a time in the range of from 1 min to 2 h, more preferably of from 5 min to 1 h, more preferably of from 10 min to 15 min.

It is to be understood that in step (a) further additives may be added. For example, in case the composition comprises at least one tonicity agent, this may be in principle added in any step of the method described above. According to one preferred embodiment, this additive, if present, is added in step (a). Thus, preferably step (a) further comprises mixing at least one tonicity agent with water, more preferably mixing glycerol with water. These additives may mixed with water prior to or after the addition of the at least one co-solvent and/or the at least one amphoteric surfactant. More preferably, these additives are mixed with water prior to or after the addition of the at least one co-solvent.

Preferably, step (a) further comprises adjusting the pH of the aqueous phase, such as through the use of buffers, such as phosphate buffers, or neutralization agents, such as sodium hydroxide, to a desired pH which is preferably in the range of from 7.0 to 10, more preferably in the range of from 8 to 10.

Step (b)

As outlined above, initially a mixture comprising EPA and DHA triglycerides is provided, wherein the EPA and DHA triglycerides may be obtained by any way known to those skilled in the art. Preferably, the oil phase is heated in step (b), that is prior to step (c), to a temperature in the range of from 30 to 70° C., more preferably from 40 to 65° C., more preferably from 50 to 60° C., more preferably to a temperature around 55° C., preferably for a time in the range of from 1 min to 30 min, more preferably from 3 min to 20 min, more preferably from 5 min to 15 min. Preferably, in step (b), the at least one co-surfactant is added. In case the oil phase is heated, the co-surfactant may be added prior to, during or after the heating step. Preferably, the co-surfactant is added during the heating step. The oil phase is preferably homogenized, preferably at a temperature in range of from 30 to 70° C., more preferably from 40 to 65° C., more preferably from 50 to 60° C., more preferably to a temperature around 55° C.

According to a preferred embodiment, at least one agent with antioxidant activity, if present, is additionally added in step (b). Thus, in this case, in step (b) optionally at least one co-surfactant and optionally at least one agent with antioxidant activity are added to the mixture of EPA triglycerides and DHA triglycerides, more preferably oleic acid and/or at least one tocopherol are added in step (b). Thus, step (b) preferably comprises providing an oil phase by mixing eicosapentaenoic acid triglycerides and docosahexaenoic acid triglycerides with the at least one co-surfactant and/or the at least one agent with antioxidant activity, wherein at least 60% by weight of the oil phase consist of eicosapentaenoic acid triglycerides and docosahexaenoic acid triglycerides. Alternatively, the provided mixture comprising EPA and DHA triglycerides may already comprise the or at least part of the total amount of the at least one co-surfactant and/or the at least one agent with antioxidant activity.

Step (c)

The method further comprises mixing the oil phase according to (b) with the aqueous phase according to (a) to give a mixture of oil phase and an aqueous phase. Preferably, thereby a pre-emulsion or an emulsion is formed. The mixing may be carried out by any methods known to those skilled in the art. Preferably, the mixing is carried out using a high shear mixer.

Preferably, the oil phase is added to the aqueous phase or vice versa at a temperature in the range of from 50 to 70° C., more preferably from 55 to 65° C.° C. Preferably the oil phase is added to the aqueous phase or vice versa at a pressure, such as under nitrogen pressure, in the range of from 0.20 to 0.80 bar, more preferably from 0.20 to 0.40 bar, such as at around 0.30 bar. During this step, pressure may be varied or held essentially constant. According to a preferred embodiment, the mixture is stirred fora time in the range of from 1 min to 1 h, preferably of from 10 min to 30 min, to give a pre-emulsion. During this step, the temperature may be varied or held essentially constant. It is to be understood that further components may also be added after the formation of the pre-emulsion. According to a preferred embodiment, the pH of the pre-emulsion is adjusted to a pH in the range of from 8 to 10, in particular by adding sodium hydroxide, if necessary.

Step (d)

Preferably, the method further comprises the homogenization of the mixture obtained from step (c). This homogenization may be carried out by any suitable methods known to those skilled in the art. Preferably, the mixture is homogenized at temperature in range of from 40 to 70° C., more preferably from 50 to 70° C., more preferably from 50 to 60° C. Preferably, the mixture is homogenized at a pressure in the range of from 400 to 600 bar, more preferably from 450 to 550 bar. During this step, the pressure may be varied or held essentially constant. During this step, the pressure may be varied or held essentially constant. Preferably, the homogenization may for example be carried out using a high pressure homogenizer or a microfluidizer.

Thus, the present invention also relates to a method as described above for preparing the inventive composition, the method further comprising:

(d) homogenizing the mixture, preferably the pre-emulsion, obtained from (c) at a temperature in the range of from 50 to 60° C. and at a pressure at a pressure in the range of from 400 to 600 bar. After the homogenization step, further steps may be carried out, such as purification steps or filtration steps.

Step (e)

Preferably, the composition obtained in (c) or (d) is heat treated, more preferably sterilized, to ensure its suitability for parenteral administration. The sterilization may be carried out by any suitable methods known to those skilled in the art. In particular, the sterilization is carried out by autoclaving, preferably at a temperature in the range of from 119° C. to 122° C., more preferably at a temperature of around 121° C., preferably fora time in the range of from 1 min to 30 min preferably of from 10 min to 15 min.

Thus, the present invention also relates to a method as described above for preparing a composition for parenteral administration as well as to a composition obtained or obtainable by said method, the method further comprising:

(e) autoclaving the mixture obtained from (c) or (d), preferably from (d), at a temperature in the range of from 119° C. to 122° C. fora time in the range of from 10 min to 15 min.

It is to be understood that the preparation of the composition preferably takes place under GMP standardized conditions in order to ensure quality, safety and effectiveness of the composition when used as a medicament or in parenteral nutrition. Further criteria for an ingredient or a composition being pharmaceutically acceptable can be derived from approval regulations by a regulatory agency and/or generally recognized pharmacopoeias. It is to be understood that the composition of the present invention is administered in an effective amount, in particular in a therapeutically effective amount, i.e. in an amount which allows for the treatment of a disease as disclosed above. Whether an amount of the composition is effective or not can be determined by the skilled person without further ado.

Methods of Treatment

In a further aspect, the invention relates to a method of treating a tumor, preferably a solid tumor, comprising the administration of the compositions according to the invention disclosed above and the administration of at least one anticancer agent. Preferably, the administration of the composition according to the invention and/or the administration of the at least one anticancer agent is a parenteral administration. The administration of the compositions according to the present invention is furthermore preferably carried out prior to, simultaneous with or after the administration of the at least one anticancer agent. Preferably, the composition according to the invention is administered in an effective amount. More preferably the composition according to the invention is administered in an effective amount to enhance the efficacy of the at least one anticancer agent. The composition according to the invention and the at least one anticancer agent is preferably administered to a mammal, more preferably to a human.

All features and preferred embodiments disclosed above in regard to the composition according to the present invention, as well as their combinations, are explicitly referred to regarding the methods of treatment according to the present invention.

Medicaments

In a further aspect, the invention relates to a medicament comprising the composition and at least one anticancer agent as disclosed above. Preferably the medicament is a medicament for the treatment of a tumor, more preferably a solid tumor.

In particular and in a further aspect the present invention thus relates to a composition comprising an aqueous phase, an oil phase, EPA and DHA and at least one anticancer agent as a medicament, wherein EPA and DHA are present in an amount of at least 65% based on the total weight of the oil phase and the at least one anticancer agent is present in a suboptimal amount. Preferably, the medicament is a medicament for the treatment of tumors, more preferably solid tumors. Most preferably, the medicament is a medicament for parenteral administration. The term "suboptimal amount" refers to an amount of the anticancer agent which results in a dose to be administered to the patient that is lower than the standard dose.

All features and preferred embodiments disclosed above in regard to the composition according to the present invention, as well as their combinations, are explicitly referred to regarding the medicament according to the preset invention.

Embodiments

In the following, especially preferred embodiments of the present invention are described by way of example:

1 Composition comprising an aqueous phase, an oil phase, EPA and DHA for use in the treatment of solid tumors, wherein EPA and DHA are present in an amount of at least 65% based on the total weight of the oil phase and wherein the treatment comprises administering the composition and administering at least one anticancer agent.
2 Composition according to embodiment 1, wherein the composition comprises EPA and DHA in a weight ratio between 6:1 and 4:1.
3 Composition according to embodiment 1 or 2 wherein the composition comprises EPA and DHA in a weight ratio between 6:1 and 4.5:1.
4 Composition according to embodiment 1, wherein the composition comprises EPA and DHA in a weight ratio between 1:2 and 1:4.
5 Composition according to any of the preceding embodiments, wherein the composition is a composition for parenteral administration and the treatment comprises parenterally administering the composition and/or the at least one anticancer agent.
6 Composition according to any of the preceding embodiments, wherein the composition is a liquid composition.
7 Composition according to any of the preceding embodiments, wherein the treatment comprises administering the composition prior to or simultaneously with the at least one anticancer agent.
8 Composition according to any of embodiments 1 to 7, wherein the treatment comprises administering the composition prior to the at least one anticancer agent.
9 Composition according to any of embodiments 1 to 7, wherein the treatment comprises administering the composition simultaneously with the at least one anticancer agent.
10 Composition according to any of the preceding embodiments, wherein the composition comprises 5 to 30% by weight of the oil phase and less than 1% by weight medium chain triglycerides, based on the total weight of the composition.
11 Composition according to any of the preceding embodiments, wherein the composition further comprises at least one amphoteric surfactant.
12 Composition according to any of the preceding embodiments, wherein the composition further comprises at least one co-surfactant.
13 Composition according to any of the preceding embodiments, wherein the composition further comprises at least one co-solvent.
14 Composition according to any of the preceding embodiments, wherein the composition further comprises at least one amphoteric surfactant, at least one co-surfactant and at least one co-solvent, and wherein the composition preferably comprises less than 0.03% by weight of sodium oleate, based on the total weight of the composition.
15 Composition according to any of the preceding embodiments, wherein the composition further comprises at least one tonicity agent.
16 Composition according to any of the preceding embodiments 1 to 14, wherein the composition further comprises at least one antioxidant.
17 Composition according to embodiments 1 to 14, wherein the composition further comprises at least one tonicity agent and at least one antioxidant.

18 Composition according to embodiments 15 or 17, wherein the at least one tonicity agent is glycerol.

19 Composition according to embodiments 16 or 17, wherein the at least one antioxidant is tocopherol.

20 Composition according to any of the preceding embodiments, wherein the composition enhances the efficacy of the at least one anticancer agent.

21 Composition according to any of the preceding embodiments, wherein the at least one anticancer agent comprises a kinase inhibitor, a receptor tyrosine kinase inhibitor, an alkylating agent, an antimetabolite, a topoisomerase inhibitor, a cytostatic antibiotic, a DNA intercalator, a mitosis inhibitor, a hormone, a hormone receptor agonist, a hormone antagonist, a radioactive agent, a photodynamic agent, an immunomodulator, a proteasome inhibitor, an antibody or an agent selected from the group consisting of arsen trioxide, asparaginase, hydroxycarbamide, miltefosin, tretinoin, alitretinoin, bexaroten, thalidomide, lenalidomide and mifamurtide.

22 Composition according to any of the preceding embodiments, wherein the at least one anticancer agent comprises a kinase inhibitor, an antimetabolite, an alkylating agent, a topoisomerase inhibitor, a mitosis inhibitor, a cytostatic antibiotic and/or a DNA intercalator, a hormone antagonist or an antibody.

23 Composition according to any of the preceding embodiments, wherein the at least one anticancer agent comprises a kinase inhibitor selected from the group consisting of sunitinib, sorafenib, imatinib, dasatinib, erlotinib, gefitinib, lapatinib, ibrutinib, vemurafenib, afatinib, axitinib, bosutinib, cabozantinib, crizotinib, nilotinib, pazopanib, pegabtanib, ponatinib, regorafenib, bosutinib, trametinib and temsirolimus.

24 Composition according to any of the preceding embodiments, wherein the at least one anticancer agent comprises an antimetabolite selected from the group consisting of methotrexate, pralatrexate, pemetrexed, cladribine, fludarabine, nelarabine, mercaptopurine, tioguanine, pentostatine, fluoruracil, tegafur, capecitabine, cytarabine, decitabine, azacytidine, floxuridine and gemcitabine.

25 Composition according to any of the preceding embodiments, wherein the at least one anticancer agent comprises an alkylating agent selected from the group consisting of cyclophosphamide, ifosfamide, trofosfamide, melphalan, chlorambucil, thiotepa, busulfane, treosulfane, bendamustine, carmustine, lomustine, nimustine, cisplatin, carboplatin, oxaliplatin, streptozotocin, procarbazine, dacarbazine, trabectedine and temozolomide.

26 Composition according to any of the preceding embodiments, wherein the at least one anticancer agent comprises a topoisomerase inhibitor selected from the group consisting of topotecan, irinotecan, teniposide, HU-331, etoposide and etoposide phosphate.

27 Composition according to any of the preceding embodiments, wherein the at least one anticancer agent comprises a mitosis inhibitor is selected from the group consisting of vincristine, vinblastine, vindesine, vinorelbine, vinflunin, eribulin, estramustine, ixabepilone, cabacitaxel, paclitaxel and docetaxel.

28 Composition according to any of the preceding embodiments, wherein the at least one anticancer agent comprises a cytostatic antibiotic and/or a DNA intercalator selected from the group consisting of dactinomycine, dexrazosan, daunorubicine, idarubicine, doxorubicine, epirubicine, mitoxantrone, amsacrine, bleomycine and mitomycine.

29 Composition according to any of the preceding embodiments, wherein the at least one anticancer agent comprises a hormone antagonist selected from the group consisting of anastrozole, letrozole, exemestane, tamoxifene, toremifene, fulvestrant, abarelix, degarelix, cyproterone acetate, nilutamide, bicalutamide and flutamide.

30 Composition according to any of the preceding embodiments, wherein the at least one anticancer agent comprises a hormone agonist selected from the group consisting of tamoxifen, medroxy-progesteron, megestrol, estramustin, buserelin, goserelin, leuprorelin, triptorelin and histrelin.

31 Composition according to any of the preceding embodiments, wherein the at least one anticancer agent comprises an antibody.

32 Composition according to any of the preceding embodiments, wherein the at least one anticancer agent comprises an antibody selected from the group consisting of bevacizumab, panitumumab, cetuximab, trastuzumab, ipilimumab, catumaxomab, ramucirumab, ertumaxomab, abituzumab, amatuximab, anetumab ravtansine, atezolizumab, codrituzumab, demcizumab, durvalumab, emibetuzumab, ensituximab, imalumab, indusatumab vedotin, lifastuzumab vedotin, lorvotuzumab mertansine, lumretuzumab, margetuximab, mirvetuximab, nivolumab, olaratumab, onutuximab, oportuzumab, patritumab, pemtumomab, pertuzumab, racotumomab, sacituzumab govitecan, seribantumab, tigatuzumab, tremelimumab, vanicizumab, dalotuzumab, ficlatuzumab, icrucumab, pembrolizumab and bavituximab.

33 Composition according to any of the preceding embodiments, wherein the treatment is a combination therapy.

34 Composition according to any of the preceding embodiments, wherein the treatment comprises the administration of at least two different anticancer agents.

35 Composition according to any of the preceding embodiments, wherein the treatment comprises the administration of at least three different anticancer agents.

36 Composition according to any of the preceding embodiments, wherein the at least one anticancer agent is administered at a dose below the standard dose of said anticancer agent.

37 Composition according to any of the preceding embodiments, wherein the at least one anticancer agent is administered at a dose of 20 to 90% of the standard dose.

38 Composition according to any of the preceding embodiments, wherein the at least one anticancer agent is administered at a dose of 30 to 80% of the standard dose.

39 Composition according to any of the preceding embodiments, wherein the at least one anticancer agent is administered at a dose of 30 to 70%, preferably 40 to 70%, of the standard dose.

40 Composition according to any of the preceding embodiments, wherein the composition is administered at a dose of 0.1 and 3.0 ml/kg body weight per day.

41 Composition according to any of the preceding embodiments, wherein the composition is administered at a dose of 0.5 and 2.5 ml/kg body weight per day.

42 Composition according to any of the preceding embodiments, wherein the composition is administered at a dose of 0.5 and 2.0, ml/kg body weight per day.

43 Composition according to any of the preceding embodiments, wherein the composition is administered at a dose of 1.0 and 2.0 ml/kg body weight per day.

44 Composition according to any of the preceding embodiments, wherein the solid tumor is a malignant tumor.

45 Composition according to any of the preceding embodiments, wherein the solid tumor is a malignant tumor selected from the group consisting of carcinoma, sarcoma, adenocarcinoma and squamous cell carcinoma.

46 Composition according to any of the preceding embodiments, wherein the solid tumor is an adenocarcinoma or a squamous cell carcinoma.
47 Composition according to any of the preceding embodiments, wherein the solid tumor is an adenocarcinoma.
48 Composition according to any of the preceding embodiments, wherein the solid tumor is selected from the group consisting of colorectal cancer, stomach cancer, breast cancer, lung cancer, mesothelioma, melanoma, oesophagus cancer, biliary cancer, endometrium cancer, cervical cancer, ovarial cancer, pancreatic cancer, prostate cancer, thyroid cancer, skin cancer, liver cancer, bladder cancer, kidney cancer, gastrointestinal stroma tumors (GIST), head and neck cancer, neuroendocrine tumors, osteosarcoma, vaginal cancer, cns tumors, soft tissue sarcoma and cancer of unknown primary (CUP).
49 Composition according to any of the preceding embodiments, wherein the solid tumor is selected from the group consisting of colorectal cancer, breast cancer, lung cancer, ovarian cancer and pancreatic cancer.
50 Composition according to any of the preceding embodiments, wherein the solid tumor is selected from the group consisting of colorectal cancer or breast cancer.
51 Composition according to any of the preceding embodiments, wherein the solid tumor is colon cancer.
52 Composition according to any of the preceding embodiments, wherein the solid tumor is a colorectal cancer.
53 Composition according to any of the preceding embodiments, wherein the solid tumor is a colorectal cancer selected from the group consisting of colon carcinoma, carcinoma of the small intestine and carcinoma of the rectum.
54 Composition according to any of the preceding embodiments, wherein the solid tumor is a colon carcinoma.
55 Composition according to any of the preceding embodiments, wherein the solid tumor is a colon carcinoma selected from the group consisting of adenocarcinoma, carcinoid and sarcoma.
56 Composition according to any of the preceding embodiments, wherein the solid tumor is a colon adenocarcinoma.
57 Composition according to any of the preceding embodiments, wherein the tumor is located in the colon ascendens, the colon transversum, the colon descendens or the colon sigmoideum.
58 Composition according to any of the preceding embodiments, wherein the solid tumor is in stage I, IIa, IIb, IIc, IIIa, IIIb, IIIc, IVa or IVb.
59 Composition according to any of the preceding embodiments, wherein the solid tumor is in stage IIa, IIIb, IVa or IVb.
60 Composition according to any of the embodiments 1 to 50, wherein the solid tumor is breast cancer selected from the group consisting of carcinoma in situ, invasive ductal carcinoma, invasive lobular carcinoma and medullar carcinoma, preferably wherein the breast cancer is an invasive ductal or lobular carcinoma.
61 Composition according to any of the embodiments 1 to 50 and 60, wherein the solid tumor is hormone receptor positive breast cancer.
62 Composition according to any of the embodiments 1 to 50 and 60, wherein the solid tumor is hormone receptor positive breast cancer.
63 Composition according to any of the embodiments 1 to 50 and 60, wherein the solid tumor is HER2 positive breast cancer.
64 Composition according to any of the embodiments 1 to 50 and 60, wherein the solid tumor is HER2 negative breast cancer.
65 Composition according to any of the embodiments 1 to 49, wherein the solid tumor is lung cancer selected from the group consisting of small cell lung cancer (SCLC) and non-small cell lung cancer (NSCLC).
66 Composition according to any of the embodiments 1 to 49 and 65, wherein the solid tumor is non-small cell lung cancer (NSCLC) selected from the group consisting of adenocarcinoma, squamous cell carcinoma and large cell lung carcinoma.
67 Composition according to any of the embodiments 1 to 50 and 65 to 66, wherein the solid tumor is non-small cell lung cancer (NSCLC) selected from the group consisting of adenocarcinoma or a squamous cell carcinoma.
68 Composition according to any of the embodiments 1 to 49 and 65 to 67, wherein the solid tumor exhibits an activating EGFR mutation.
69 Composition according to any of the embodiments 1 to 49 and 65 to 68, wherein the lung cancer is in stage in stage II, III or IV.
70 Composition according to any of the embodiments 1 to 49, wherein the solid tumor is ovarian cancer selected from the group consisting of malignant epithelial tumors, malignant germ band and/or stromal tumors, malignant germ cell tumors and borderline tumors.
71 Composition according to any of the embodiments 1 to 49, wherein the solid tumor is a pancreatic cancer selected from the group consisting of tumors of the connective tissue, carcinoma of the exocrine pancreas and carcinoma of the endocrine pancreas.
72 Composition according to any of the embodiments 1 to 49 and 71, wherein the solid tumor is an exocrine pancreas carcinoma selected from the group consisting of adenocarcinoma, cystadenocarcinoma and signet ring cell carcinoma.
73 Composition according to any of the embodiments 1 to 49 and 71, wherein the solid tumor is an endocrine pancreas carcinoma selected from the group consisting of malignant insulinoma, glucagonoma, gastrinoma, VIPoma and somatostatinoma.
74 Composition according to any of the embodiments 1 to 49 and 71, wherein the solid tumor is a tumor of the pancreatic connective tissue selected from the group consisting of sarcoma and lymphoma.
75 Composition comprising an aqueous phase, an oil phase, EPA and DHA and at least one anti-cancer agent as a medicament, wherein EPA and DHA are present in an amount of at least 65% based on the total weight of the oil phase and wherein the at least one anticancer agent is present in a suboptimal amount.
76 Composition according to embodiment 75, wherein the medicament is a medicament for the treatment of tumors.
77 Composition according to any of embodiments 75 or 76, wherein the medicament is a medicament for the treatment of solid tumors.
78 Method of treating a tumor comprising administering a composition comprising the components according to any of embodiments 1 to 4 or 10 to 19 and at least one anticancer agent.
79 Method according to embodiment 78, wherein the at least one anticancer agent is an anticancer agent according to any of the embodiments 21 to 32.
80 Method according to embodiment 78 or 79, wherein the tumor is a solid tumor.

81 Method according to any of the embodiments 78 to 80, wherein the tumor is a tumor according to any of the embodiments 44 to 74.
82 Method according to any of the embodiments 78 to 81, wherein composition is administered to a mammal.
83 Method according to any of the embodiments 78 to 82, wherein composition is administered to a human.
84 Kit of parts comprising a composition according to any of the embodiments 1 to 19 and at least one anticancer agent according to any of the embodiments 21 to 32.

The following examples are intended to illustrate the present invention without limiting it.

EXAMPLES

Different mixtures comprising highly concentrated omega-3 fatty acids (eicosapentaenoic acid (EPA) and docosahexaenoic acid (DHA)) as triglycerides as obtained from Solutex S.L were used:

Mixture 1 comprised 0.63 g/g EPA triglyceride and 0.14 g/g DHA triglyceride. Mixture 2 comprised 0.20 g/g EPA triglyceride and 0.46 g/g DHA triglyceride.

Example 1

General Procedure A for the Preparation of an Emulsion According to the Invention Using a shear mixer, lecithin (PL90, obtainable from egg yolk=egg lecithin with a phosphatidylcholine content of 64-79% and a phosphatidylethanolamine content of 10-18% by weight) was dispersed in water for injection, at a temperature between 55-60° C., previously containing glycerol and polyethylene glycol (PEG), using a Rayneri TURBOTEST high shear mixer, until a homogeneous dispersion was obtained. Afterwards, the pH of the aqueous dispersion was adjusted to 9-10. The oil phase, containing different ratios of docosahexaenoic acid/eicosapentanoic acid triglycerides (mixtures 1 and 2), was heated to 55° C. and, then, oleic acid was added until a clear and homogeneous solution was obtained. The aqueous dispersion was then transferred to a separate container and the oil phase was added under continuous stirring, using a Rayneri TURBOTEST high shear mixer, to obtain coarse oil-in-water emulsions with oil phase concentrations comprised between 10-30 wt. The coarse emulsions were then passed six times through a homogenizer (Niro Soavi Panda Plus 2000) at 500 bar and a temperature between 50-60° C. Finally, the emulsions were autoclaved at 122° C. for 15 min. Final lipid emulsions were obtained. The mean particle size of the lipid emulsions was measured using a Malvern Mastersizer 2000.

TABLE 1

Composition of a formulation prepared according to example 1

| Ingredients | Weight-% |
|---|---|
| Triglyceride - EPA/DHA | 10 |
| Egg lecithin | 1.2 |
| Oleic acid | 0.15 |
| Glycerol | 2.25 |
| Polyethylene glycol PEG 400 | 1.0 |
| Water for injection | adds up to 100 |
| Properties | |
| pH release | 8-8.7 |
| Surface mean droplet diameter D [3.2] | ≤0.3 μm |
| Volume weighted mean diameter D [4.3] | ≤0.3 μm |
| % Droplets >5 μm | ≤0.05 |

Further compositions prepared are given in Table 2. For some of these compositions, no stable emulsions could be obtained. Surprisingly, in particular emulsions comprising a combination of PEG, oleic acid and lecithin turned out to be particularly stable.

TABLE 2

Examples of compositions tested and some relevant parameters

| Composition | 1 a, b | 2 a, b | 3 a, b | 4 a, b | 5 a, b | 6 a, b | 7 a, b |
|---|---|---|---|---|---|---|---|
| DHA/EPA [weight.-%] | 10 Mixtures 1, 2 | 10 Mixtures 1, 2 | 10 Mixtures 1, 2 | 10 Mixtures 1, 2 | 10 Mixtures 1, 2 | 10 Mixtures 1, 2 | 10 Mixtures 1, 2 |
| Egg lecithin [weight.-%] | 1.2 | 1.2 | 1.2 | 1.2 | 1.2 | 1.2 | 1.2 |
| Glycerol [weight.-%] | 2.25 | 2.25 | 2.5 | 2.5 | 2.5 | 2.25 | 2.5 |
| Tocopherols [weight.-%] | 0.02 | 0.02 | 0.02 | 0.02 | 0.02 | 0.02 | 0.02 |
| Oleic Acid [weight.-%] | 0.15 | 0.15 | — | — | — | 0.15 | 0.12 |
| Sodium Oleate [weight.-%] | — | — | 0.2 | 0.3 | 0.03 | — | 0.18 |
| PEG 400 [weight.-%] | 1 | 2 | — | — | — | — | — |
| Propylene glycol [weight.-%] | — | — | — | — | — | 1 | — |
| Water for injection [weight.-%] | Adds up to 100 | Adds up to 100 | Adds up to 100 | Adds up to 100 | Adds up to 100 | Adds up to 100 | Adds up to 100 |
| Stable Emulsion Y = yes; N = no | Y | Y | N After some weeks | N After some weeks | N After some weeks | Y | N spontaneous |

TABLE 2-continued

Examples of compositions tested and some relevant parameters

| Composition | 1 a, b | 2 a, b | 3 a, b | 4 a, b | 5 a, b | 6 a, b | 7 a, b |
|---|---|---|---|---|---|---|---|
| pH release | 8.7 | 8.8 | 8.6 | 9.4 | 8.5 | 8.6 | 8.8 |
| Surface mean droplet diameter D [3, 2] µm | ≤0.3 | ≤0.3 | ≤0.3 | ≤0.3 | ≤0.3 | ≤0.3 | >0.03 |
| Volume weighted mean diameter D [4, 3] µm | ≤0.3 | ≤0.3 | ≤0.3 | ≤0.3 | ≤0.3 | ≤0.3 | >0.03 |
| % Droplets > 5 µm | ≤0.05 | ≤0.05 | >0.05 | >0.05 | >0.05 | ≤0.05 | >0.05 |

Example 2

Effect of EPA and DHA on the Efficacy of Irinotecan in a Subcutaneous SW620 Xenograft Model Animals A group of 168 female BALB/c nude mice was used. The mice's body weight was 19-24 g. The mice were kept in individual ventilated cage (IVC) systems at c constant temperature of about 23° C. The diet consisted of sterilized and $Co^{60}$ irradiated dry granule food ad libitum.

Cell Culture

Tumor cells of the human caucasian colon adenocarcinoma cell line SW620 were maintained in vitro as a monolayer culture in L-15 medium (Gibco) supplemented with 10% fetal bovine serum (Gibco) at 37° C. . The tumor cells were routinely subcultured 2-3 times weekly by trypsin-EDTA (Gibco) treatment with a general splitting factor of 1:3. Cells in an exponential growth phase were harvested and counted for tumor inoculation.

Cells were used for inoculation when they reached a confluence of about 80%. They were washed with PBS, trypsinized with 5 ml trypsin/EDTA and incubated for 3-5 min at RT. The number of living cells was determined using a Neubauer counting chamber and trypan blue staining (1:6).

Inoculation and Group Assignment $5 \times 10^6$ living SW620 cells in 100 µl PBS were used per mouse. Each mouse was inoculated sub-cutaneously at the right flank region for tumor development on day 0. Tumor volume was monitored using a caliper and treatment was started when the mean tumor volume reached 154 $mm^3$.

Mice were assigned into groups using randomized block design based on their tumor volumes in order to ensure that the groups had comparable baselines. Animals were first divided into homogeneous blocks according to their initial tumor size. Secondly, within each block randomization of experimental animals to treatments was conducted in order to minimize systematic error.

Determination of a Non-Effective, an Optimal and a Suboptimal Dose

The suboptimal dose of irinotecan (Dalian Meilun Biotech Co., LTD) was determined by testing of the following doses of the anticancer agent: 2, 7, 20, 25, 100 mg/kg. A dose of 2 mg/kg could be identified as non-effective. A dosage of 7 mg/kg could be identified as optimal. A dose of 4 mg/kg was defined as a suboptimal dose. In the following, doses of 2 mg/kg (non-effective) and 4 mg/kg (suboptimal) were used.

Treatment of Inoculated Mice

The groups of mice were treated with irinotecan alone (Groups 5 and 9), with compositions 1a and 1b (see Table 2 above) alone (Groups 2 and 3) and with a combination of irinotecan and compositions 1a and 1b, respectively (Groups 6, 7, 10 and 11) over a course of more than 21 days.

In addition, a further composition (Omegaven 10%; Fresenius Kabi) was tested either alone (Group 4) or in combination with the suboptimal dose of irinotecan (Group 8). Omegaven 10% is an emulsion like compositions 1a or 1b and had a concentration of about 2.04 g/g EPA and 2.27 g/g DHA.

A control group of mice (Group 1) was treated with a vehicle control (saline) only.

Saline, composition 1a, 1b and Omegaven 10% were administered intravenously, irinotecan was administered intraperitonealy. The groups of mice were treated according to the following Table 3.

TABLE 3

Treatment of inoculated mice

| Group | Treatment | Dose | Doses administered |
|---|---|---|---|
| 1 | Saline | 2 ml/kg | Day 7-11, 14-18, 21-24 |
| 2 | Composition 1a | 2 ml/kg | Day 7-11, 14-18, 21-25 |
| 3 | Composition 1b | 2 ml/kg | Day 7-11, 14-18, 21-25, 28-29 |
| 4 | Omegaven 10% | 2 ml/kg | Day 7-11, 14-18, 21-24 |
| 5 | Irinotecan | 4 mg/kg | Q4D x 6 |
| 6 | Composition 1a | 2 ml/kg | Day 7-11, 14-18, 21-25, 28-30 |
|   | Irinotecan | 4 mg/kg | Q4D x 6 |
| 7 | Composition 1b | 2 ml/kg | Day 7-11, 14-18, 21-25, 28-30 |
|   | Irinotecan | 4 mg/kg | Q4D x 6 |
| 8 | Omegaven 10% | 2 ml/kg | Day 7-11, 14-18, 21-25, 28-29 |
|   | Irinotecan | 4 mg/kg | Q4D x 6 |
| 9 | Irinotecan | 2 mg/kg | Q4D x 6 |
| 10 | Composition 1a | 2 ml/kg | Day 7-11, 14-18, 21-25, 28-30 |
|   | Irinotecan | 2 mg/kg | Q4D x 6 |
| 11 | Composition 1b | 2 ml/kg | Day 7-11, 14-18, 21-25, 28-30 |
|   | Irinotecan | 2 mg/kg | Q4D x 6 |

The date of tumor cell inoculation was denoted as day 0. Thus, the number of days refer to the days after inoculation. Q4D refers to an administration every four days (1 day dosing and 3 days off). Dosing volume was adjusted based on body weight. For irinotecan the dosing volume was 10 ml/kg.

Tumor Growth Inhibition

Tumor volumes were measured twice weekly in two dimensions using a caliper and the volume was expressed in $mm^3$ using the formula $V=0.5 \, a \times b^2$, wherein a and b were the long and short diameters of the tumor, respectively.

The tumor volumes and tumor growth inhibition (TGI) at day 21 in comparison to the control is given in Table 4 below. The results were statistically analyzed for significance.

TABLE 4

Tumor volume and tumor growth inhibition at day 21

| Group | Treatment | Tumor volume [mm³] | TGI [%] |
|---|---|---|---|
| 1 | Saline | 1829 | N/A |
| 2 | Composition 1a | 1669 | 9 |
| 3 | Composition 1b | 1481 | 19 |
| 4 | Omegaven 10% | 1849 | −1 |
| 5 | Irinotecan (4 mg/kg) | 731 | 60 |
| 6 | Composition 1a + Irinotecan (4 mg/kg) | 629 | 66 |
| 7 | Composition 1b + Irinotecan (4 mg/kg) | 715 | 61 |
| 8 | Omegaven 10% + Irinotecan (4 mg/kg) | 734 | 60 |
| 9 | Irinotecan (2 mg/kg) | 1200 | 34 |
| 10 | Composition 1a + Irinotecan (2 mg/kg) | 1049 | 43 |
| 11 | Composition 1b + Irinotecan (2 mg/kg) | 1034 | 43 |

As can be taken from Table 4 the combined administration of a composition according to the invention significantly enhanced the efficacy of Irinotecan. In particular, if irinotecan was administered at a suboptimal dose (Group 5), the combined administration with a composition according to the invention (Group 6 or 7) led to an increased TGI demonstrating the enhancement of the efficacy of the anticancer agent.

Contrasting this, a combined administration with an EPA:DHA ratio other than the ratio according to the invention (Group 8) even led to an increase of the tumor volume compared to the sole administration of Irinotecan thus demonstrating a possible reduction of the efficacy of the anticancer agent.

As evidenced by Groups 10 and 11, the compositions according to the invention showed an enhancement of the efficacy of the anticancer agent even when the latter was administered at a non-effective dose (Group 9).

Example 2 was repeated with similar results exchanging compositions 1a and 1b for compositions 2a and 2b and 6a and 6b, respectively according to Table 2.

Example 3

Effect of EPA and DHA on the Efficacy of Fluorouracil in a Subcutaneous LS174T Xenograft Model Example 2 was repeated with the anticancer agent fluorouracil (5-FU) and utilizing a different xen-ograft model involving the human caucasian colon adenocarcinoma cell line LS174T.

The suboptimal dose of 5-FU was determined with 75 mg/kg. The anticancer agent was intraperitoneally administered at the suboptimal dose once a week (days 11, 18 and 25 after inoculation). The emulsions were administered intravenously five times a week (Mo-Fr) at a dose of 2 ml/kg.

The tumor volumes and TGI on day 28 in comparison to the control is given in Table 5 below. The results were statistically analyzed.

TABLE 5

Tumor volume and tumor growth inhibition at days 28

| | Saline | Composition 1a + 5-FU | Composition 1b + 5-FU | Omegaven 10% + 5-FU |
|---|---|---|---|---|
| Tumor volume [mm³] | 903 | 644 | 561 | 747 |
| TGI [%] | N/A | 29 | 38 | 17 |

As can be taken from Table 5 the combined administration of a composition according to the invention significantly enhanced the efficacy of 5-FU. In particular, if 5-FU was administered at a suboptimal dose, the combined administration with a composition according to the invention led to an increased TGI demonstrating the enhancement of the efficacy of the anticancer agent.

Example 3 was repeated with similar results exchanging compositions 1a and 1b for compositions 2a and 2b and 6a and 6b, respectively according to Table 2.

The invention claimed is:

1. Composition comprising an aqueous phase, an oil phase, eicosapentaenoic acid (EPA) and docosahexaenoic acid (DHA) for use in the treatment of solid tumors, wherein the treatment comprises administering the composition and administering at least one anticancer agent,
the composition characterized in that
EPA and DHA are present in an amount of at least 65% based on the total weight of the oil phase and
wherein the composition comprises EPA and DHA in a weight ratio between 6:1 and 4:1, or wherein the composition comprises EPA and DHA in a weight ratio between 1:2 and 1:4.

2. The composition according to claim 1, wherein the composition comprises 5 to 30% by weight of the oil phase and less than 1% by weight medium chain triglycerides, based on the total weight of the composition.

3. The composition according to claim 1, wherein the composition further comprises at least one amphoteric surfactant, at least one co-surfactant and at least one co-solvent, and wherein the composition comprises less than 0.03% by weight of sodium oleate, based on the total weight of the composition.

4. A method of treating a solid tumor, said method comprising administering a composition according to claim 1 and administering at least one anticancer agent.

5. The composition according to claim 1, wherein the at least one anticancer agent comprises a kinase inhibitor, a receptor tyrosine kinase inhibitor, an alkylating agent, an antimetabolite, a topoisomerase inhibitor, a cytostatic antibiotic, a DNA intercalator, a mitosis inhibitor, a hormone, a hormone receptor agonist, a hormone antagonist, a radioactive agent, a photodynamic agent, an immunomodulator, a proteasome inhibitor, an antibody or an agent selected from the group consisting of arsen trioxide, asparaginase, hydroxycarbamide, miltefosin, tretinoin, alitretinoin, bexaroten, thalidomide, lenalidomide and mifamurtide.

6. The composition according to claim 1, wherein the at least one anticancer agent comprises a kinase inhibitor, an antimetabolite, an alkylating agent, a topoisomerase inhibitor, a mitosis inhibitor, a cytostatic antibiotic and/or a DNA intercalator, a hormone antagonist or an antibody.

7. The composition according to claim 1, wherein the at least one anticancer agent is administered at a dose below the standard dose of said anticancer agent.

8. The composition according to claim 1, wherein the at least one anticancer agent is administered at a dose of 30 to 70% of the standard dose.

9. The method according to claim 4, wherein the solid tumor is a malignant tumor selected from the group consisting of carcinoma, sarcoma, adenocarcinoma and squamous cell carcinoma.

10. The method according to claim 4, wherein the solid tumor is selected from the group consisting of colorectal cancer, stomach cancer, breast cancer, lung cancer, mesothelioma, melanoma, oesophagus cancer, biliary cancer, endometrium cancer, cervical cancer, ovarian cancer, pancreatic cancer, prostate cancer, thyroid cancer, skin cancer, liver cancer, bladder cancer, kidney cancer, gastrointestinal stromal tumors (GIST), head and neck cancer, neuroendocrine tumors, osteosarcoma, vaginal cancer, CNS tumors, soft tissue sarcoma and cancer of unknown primary (CUP).

11. The method according to claim 4, wherein the solid tumor is a colon adenocarcinoma or breast cancer.

12. A composition comprising an aqueous phase, an oil phase, EPA and DHA and at least one anticancer agent as a medicament, wherein the at least one anticancer agent is present in a suboptimal amount,
  the composition characterized in that EPA and DHA are present in an amount of at least 65% based on the total weight of the oil phase and
  wherein the composition comprises EPA and DHA in a weight ratio between 6:1 and 4:1, or wherein the composition comprises EPA and DHA in a weight ratio between 1:2 and 1:4.

13. The composition according to claim 12, wherein the medicament is a medicament for the treatment of tumors.

14. The method according to claim 4, wherein the at least one anticancer agent is present in a suboptimal amount.

15. The method according to claim 4, wherein the composition is administered, prior to, or simultaneously with, or after administration of, the at least one anticancer agent.

16. The method according to claim 4, wherein the composition is administered, parenterally.

* * * * *